United States Patent [19]

Davidson

[11] Patent Number: 4,604,243

[45] Date of Patent: Aug. 5, 1986

[54] ARYLATION OF OLEFINS

[75] Inventor: Robert I. Davidson, Baton Rouge, La.

[73] Assignee: Ethyl Corporation, Richmond, Va.

[21] Appl. No.: 758,818

[22] Filed: Jul. 25, 1985

[51] Int. Cl.$^4$ .................. C07C 121/66; C07C 69/612
[52] U.S. Cl. .................... 558/388; 548/197; 548/202; 546/180; 546/346; 560/9; 560/20; 560/47; 560/55; 560/81; 560/105; 562/426; 562/438; 562/456; 562/465; 562/496; 564/442; 568/316; 568/433; 568/649; 568/655; 570/191; 570/194
[58] Field of Search ............. 260/465 G; 560/55, 105; 570/191, 194

[56] References Cited

PUBLICATIONS

Doyle et al., J. Org. Chem., vol. 42, pp. 2431-2436, (1977).
Kawamatsu et al., Arzneim.-Forsch./Drug Res., vol. 30(I), No. 5, pp. 751-758, (1980).
Rondestvedt, Jr., Organic Reactions, vol. 11, pp. 189-260.
Rondestvedt, Jr., Organic Reactions, vol. 24, pp. 225-259.

*Primary Examiner*—Dolph H. Torrence
*Attorney, Agent, or Firm*—Donald L. Johnson; John F. Sieberth; Patricia J. Hogan

[57] ABSTRACT

An olefin, especially an activated olefin, is arylated by reaction with an arylamine, such as an aniline, in an inert polar organic solvent and in the presence of an alkyl nitrite, a hydrogen halide, and a catalytic amount of a copper catalyst having the copper in an oxidation state below +2.

18 Claims, No Drawings

ARYLATION OF OLEFINS

FIELD OF INVENTION

This invention relates to a process for arylating olefins and more particularly to a process for adding halogen and an aryl group to the double bond of an olefin.

BACKGROUND

It is known that olefins, especially activated olefins, can be arylated by a conventional two-step Meerwein arylation reaction wherein an arylamine is converted to a diazonium salt, which is then reacted with the olefin in the presence of a copper catalyst, usually cupric chloride.

It is also known that arylated products can be obtained by a one-step Meerwein-type reaction wherein the olefin is treated directly with the arylamine and a nitrite rather than with a diazonium salt. Doyle et al., *J. Org. Chem.*, Vol. 42, 1977, pp. 2431–2436, show that such a one-step Meerwein reaction can be conducted by reacting an arylamine with a large excess of an olefin in an inert polar solvent and in the presence of superstoichiometric amounts of an alkyl nitrite and anhydrous cupric chloride. Kawamatsu et al., *Arzneim.-Forsch./Drug Res.*, Vol. 30(I), No. 5, 1980, pp. 751–758, show that it is possible to conduct such a reaction by reacting an arylamine with an excess of an olefin in an aqueous organic solvent and in the presence of HCl, an inorganic nitrite, and cuprous oxide.

In all of these types of Meerwein reactions, it has been found that the presence of electron-donating groups on the arylamine has generally decreased reactivity and that the product yields obtainable from such arylamines, as well as from other arylamines, could bear improvement.

SUMMARY OF INVENTION

An object of this invention is to provide a novel process for arylating olefins.

Another object is to provide such a process wherein the arylated olefins are obtained in improved yields by a one-step Meerwein reaction.

These and other objects are attained by reacting an arylamine with an olefin in an inert polar organic solvent and in the presence of an alkyl nitrite, a hydrogen halide, and a catalytic amount of a copper catalyst having the copper in an oxidation state below +2.

DETAILED DESCRIPTION

Arylamines that can be used in the process of the invention may be generally described as the arylamines already known to be capable of being used in Meerwein-type arylation reactions, including those which, because of the presence of electron-donating groups on the ring, have been disappointing in the degree of reactivity they have shown in the known reactions. Such arylamines are compounds having an amino group attached to an aromatic (e.g., phenyl, naphthyl, pyridyl, thiazolyl, etc.) ring which optionally bears one or more other substituents, such as a chloro, fluoro, cyano, nitro, amino, substituted amino, or an optionally-substituted —R, —OR, —SR, or —COOR substituent wherein R is alkyl, cycloalkyl, or aryl. Any organic substituents on the ring generally contain up to about 40 carbons, most commonly 1–6 carbons. Arylamines having reactive substituents generally are not used unless it is intended to react each molecule of arylamine with more than one molecule of olefin.

As in the known Meerwein reactions, the arylamines, bearing electron-donating groups appear to be less reactive than the other arylamines, but their diminished reactivity is not as severe a problem as in the known reactions because of the generally improved yields obtained in the present process. Exemplary of the arylamines that can be used are aniline, 4-methoxyaniline, 3,4-dimethoxyaniline, 3,4,5-trimethoxyaniline, 4-(2-methyl-2-phenylpropyloxy)aniline, 4-nitroaniline, 4-acetylaniline, 4-chloroaniline, 2,4-dichloroaniline, 4-methylaniline, p-phenylenediamine, benzidine, p-aminobiphenyl, 3-aminoquinoline, 5-nitro-2-aminothiazole, aminonaphthalene, etc., as well as the other arylamines taught in Doyle et al., Kawamatsu et al., and the references cited therein (especially Rondestvedt, *Organic Reactions,* Vol. 11, pp. 189–260, and Rondestvedt, *Organic Reactions,* Vol. 24, pp. 225–259), all of which are incorporated herein in toto by reference.

Olefins utilizable in the process are also generally describable as those already known to be capable of being used in Meerwein-type arylation reactions. Such olefins include simple alkenes, such as ethylene, but are preferably activated olefins, i.e., olefins wherein the ethylenic bond is activated by being attached to an electron-withdrawing group, such as carbonyl, cyano, halo, aryl, vinyl, etc. Exemplary of such olefins are quinones; unsaturated nitriles, such as acrylonitrile, methacrylonitrile, ethacrylonitrile, etc.; unsaturated acids and esters, such as acrylic acid, methacrylic acid, maleic acid, cinnamic acid, etc., and their methyl, higher alkyl, cycloalkyl, and aryl esters; conjugated dienes, such as butadiene, isoprene, etc.; aryl olefins, such as styrene, 4-methylstyrene, etc.; unsaturated halides, such as vinyl chloride, vinylidene chloride, etc.; unsaturated aldehydes, such as acrolein, methacrolein, etc.; as well as the other activated olefins taught by Doyle et al., Kamawatsu et al., and the Rondestvedt references.

The amount of olefin employed should generally be in the range of about 5–40, preferably about 13–19, mol equivalents per mol equivalent of amino groups in the arylamine, since the use of too much or too little olefin tends to increase by-product formation. However, larger or smaller amounts of olefin can be used when this normally disadvantageous tendency can be tolerated.

The alkyl nitrite may be any alkyl nitrite capable of diazotizing the arylamine in situ but is generally an alkyl nitrite containing 1-6 carbons, such as the methyl, ethyl, n-propyl, isopropyl, n-butyl, isobutyl, t-butyl, isoamyl, and hexyl, etc., nitrites. It is important that the nitrite be an alkyl nitrite instead of one of the inorganic nitrites sometimes employed for diazotization, since it has been found that inorganic nitrites are not equivalent to alkyl nitrites in the present process. The amount of alkyl nitrite used should be at least the substantially stoichiometric amount, i.e., an amount slightly in excess of the amount required to react with the arylamine, and is generally in the range of about 1.25–1.5 mol equivalents per mol equivalent of amino groups in the arylamine. More alkyl nitrite can be employed without deleteriously affecting the process, but a large excess of the nitrite is unnecessary and uneconomical.

The hydrogen halide employed in the process is usually hydrogen chloride but may be another hydrogen halide, such as hydrogen bromide, hydrogen iodide, etc.

It may be incorporated by using an arylamine hydrohalide, e.g., an arylamine hydrochloride, as the arylamine or by introducing it as a gas or aqueous solution. However, because of the undesirability of incorporating enough water to serve as a co-solvent for the reaction, any aqueous solution used is desirably a concentrated acid, such as concentrated hydrochloric acid. The amount of hydrogen halide used should be at least one mol equivalent per mol equivalent of amino groups. There does not appear to be any maximum to the amount that may be employed, but economic considerations generally lead to the use of about 1–2 mol equivalents.

As mentioned above, the catalyst is a copper catalyst having the copper in an oxidation state below +2. Any such catalyst may be utilized, but the catalysts that are preferred are the more available catalysts, such as copper powder, cuprous oxide, cuprous chloride, cuprous bromide, etc. This component of the reaction mixture is employed in a catalytic amount, e.g., about 0.05–0.2, most commonly about 0.1, mol equivalent, based on the number of amino groups present, the amount of catalyst that is particularly useful varying with the reactivities of the reactants being used.

The solvents that may be employed in the reaction are inert polar organic solvents, such as acetonitrile, acetone, methyl ethyl ketone, N-methylpyrrolidone, pyridine, dimethyl sulfoxide, etc., i.e., solvents of the type conventionally used in Meerwein arylation reactions. Except for the olefin, which can have a solvating effect in addition to functioning as a reactant, the inert polar organic solvent serves as the sole solvent in the reaction mixture.

The reaction is conducted by combining the aforementioned ingredients in any convenient manner and maintaining them in contact with one another, generally with stirring, for a suitable time, e.g., about 1–3 hours. Ordinarily, it is preferred to conduct the reaction at ambient temperature, e.g., about 20°–45° C., although cooling may be used if too much heat is generated by the reaction.

The invention is advantageous as a means of providing arylated olefins in improved yields by a one-step Meerwein reaction, and it has the further advantages of requiring only a small amount of catalyst and being tolerant of substituents on the aromatic ring. The products formed by the novel Meerwein reaction are known compounds which are primarily useful as intemediates for materials such as flavorings, perfumes, cosmetics, polymers, pharmaceuticals, etc.

The following examples are given to illustrate the invention and are not intended as a limitation thereof.

EXAMPLE I

A mixture of 2.28 g (25 mmols) of distilled aniline, 30 mL of acetonitrile, 2.6 mL (31 mmols) of concentrated hydrochloric acid, 30 mL (456 mmols) of distilled acrylonitrile (AN), and 0.36 g (2.5 mmols) of cuprous oxide was stirred for five minutes under nitrogen. A mixture of 2.8 g (31 mmols) of isopropyl nitrite (IPN) and 30 mL of acetonitrile was added dropwise over a period of 20 minutes. The mixture warmed to 45° C. and nitrogen gas evolved. After stirring at ambient temperature for two hours, the dark mixture was worked up to provide an 84% yield of 2-chloro-3-phenylpropionitrile (CPPN).

EXAMPLE II

A series of reactions was conducted by essentially repeating Example I except for varying the amounts of ingredients. The amounts of other ingredients used per mol equivalent of aniline, as well as the yields of CPPN obtained are shown in Table I.

TABLE I

| Run | Amounts (Mol-Equiv.) | | | | Yield (%) |
|---|---|---|---|---|---|
| | AN | HCl | $Cu_2O$ | IPN | CCPN |
| II-A | 18 | 1.5 | 0.1 | 1.5 | 64.8 |
| II-B | 19 | 1.25 | 0.1 | 1.25 | 78.1 |
| II-C | 19 | 1.25 | 0.05 | 1.25 | 5.5 |
| II-D | 19 | 1.25 | 0.15 | 1.5 | 72.4 |
| II-E | 19 | 1.0* | 0.1 | 1.25 | 69.9 |
| II-F** | 39 | 1.25 | 0.1 | 1.25 | 79.2 |

*HCl incorporated by using aniline hydrochloride as the amine
**Reaction using only 14 mL of acetonitrile

EXAMPLE III

Two reactions were conducted by repeating Example II-E except for substituting copper powder and cuprous chloride for the cuprous oxide. The use of Cu led to a 74.1% yield of CPPN; the use of CuCl led to a yield of 70.6%.

EXAMPLE IV

A series of reactions was conducted by essentially repeating Example I except for using methyl acrylate (MA) instead of acrylonitrile and varying the amounts of ingredients as shown in Table II, which also shows the yields of methyl 2-chloro-3-phenylpropionate (MCPP) obtained.

TABLE II

| Run | Amounts (Mol-Equiv.) | | | | Yield (%) |
|---|---|---|---|---|---|
| | MA | HCl | $Cu_2O$ | IPN | MCPP |
| IV-A | 13 | 2 | 0.1 | 1.5 | 73.7 |
| IV-B | 13 | 1.5 | 0.1 | 1.5 | 77.5 |
| IV-C | 13 | 1.25 | 0.1 | 1.25 | 71.0 |
| IV-D | 13 | 1.25 | 0.05 | 1.25 | 59.0 |
| IV-E | 13 | 1.0* | 0.1 | 1.25 | 69.2 |
| IV-F** | 29 | 1.25 | 0.1 | 1.25 | 71.0 |
| IV-G | 14 | 3 | 0.075 | 1.2 | 26.1 |

*HCl incorporated by using aniline hydrochloride as the amine
**Reaction using only 15 mL of acetonitrile

EXAMPLE V

Two reactions were conducted by repeating Example IV-E except for substituting copper powder and cuprous chloride for the cuprous oxide. The use of Cu led to a 65.1% yield of MCPP; the use of CuCl led to a 74.4% yield.

EXAMPLE VI

Following the general procedure of Example I, 364 mmols of methacrylonitrile were reacted with 25 mmols of distilled aniline in 30 mL of acetonitrile and in the presence of 38 mmols of concentrated HCl and 2.5 mmols of cuprous oxide. The process resulted in an 87.9% yield of 2-chloro-2-methyl-3-phenylpropionitrile.

EXAMPLE VII

Following the general procedure of Example I, 280 mmols of distilled methyl methacrylate were reacted with 25 mmols of distilled aniline in 30 mL of acetonitrile and in the presence of 38 mmols of concentrated HCl and 2.5 mmols of cuprous oxide. The process resulted in an 80% yield of methyl 2-chloro-2-methyl-3-phenylpropionate.

EXAMPLE VIII

Following the general procedure of Example I, 236 mmols of distilled styrene were reacted with 25 mmols of distilled aniline in 30 mL of acetonitrile and in the presence of 38 mmols of concentrated HCl and 2.5 mmols of cuprous oxide. The process resulted in a 66.7% yield of 2-chloro-1,2-diphenylethane.

EXAMPLE IX

Following the general procedure of Example I, 150 mmols of maleic anhydride were reacted with 25 mmols of distilled aniline in 60 mL of acetonitrile and in the presence of 38 mmols of concentrated HCl and 2.5 mmols of cuprous oxide. The process resulted in a 29.2% yield of 3-phenylmaleic anhydride.

EXAMPLE X

Following the general procedure of Example I, 339 mmols of methyl acrylate were reacted with 25 mmols of crude 4-methoxyaniline in 30 mL of acetonitrile and in the presence of 38 mmols of concentrated HCl and 2.5 mmols of cuprous oxide. The process resulted in a 57.3% yield of methyl 2-chloro-3-(4-methoxyphenyl)-propionate.

EXAMPLE XI

Following the general procedure of Example I, 280 mmols of distilled methyl methacrylate were reacted with 25 mmols of 3,4-dimethoxyaniline in 30 mL of acetonitrile and in the presence of 42 mmols of concentrated HCl and 2.5 mmols of cuprous oxide. The process resulted in a 39.2% yield of methyl 2-chloro-2-methyl-3-(3,4-dimethoxyphenyl)propionate.

It is obvious that many variations can be made in the products and processes set forth above without departing from the spirit and scope of this invention.

What is claimed is:

1. In a process for adding halogen and an aryl group to the double bond of an olefin by reacting an arylamine with the olefin in the presence of an alkyl nitrite, a copper catalyst, and an inert polar organic solvent, the improvement which comprises conducting the reaction in the presence of at least one equivalent of a hydrogen halide and employing as the catalyst a catalytic amount of a copper catalyst having the copper in an oxidation state below +2.

2. The process of claim 1 wherein the arylamine is an aniline.

3. The process of claim 2 wherein the aniline is aniline.

4. The process of claim 2 wherein the aniline is a ring-substituted aniline.

5. The process of claim 1 wherein the olefin is an activated olefin.

6. The process of claim 5 wherein the activated olefin is methyl acrylate.

7. The process of claim 5 wherein the activated olefin is acrylonitrile.

8. The process of claim 1 wherein the catalyst is selected from copper powder, cuprous oxide, cuprous chloride, and cuprous bromide.

9. The process of claim 8 wherein the catalyst is cuprous oxide.

10. The process of claim 1 wherein the hydrogen halide is hydrogen chloride.

11. The process of claim 1 wherein aniline is reacted with methyl acrylate in the presence of hydrogen chloride and the copper catalyst.

12. The process of claim 1 wherein aniline is reacted with acrylonitrile in the presence of hydrogen chloride and the copper catalyst.

13. The process of claim 1 wherein the arylamine is reacted with about 5–40 mol equivalents of the olefin per mol equivalent of amino groups in the arylamine.

14. The process of claim 13 wherein the amount of olefin is in the range of about 13–19 mol equivalents.

15. The process of claim 1 wherein the reaction is conducted in the presence of about 0.05–0.2 mol equivalent of the catalyst per mol equivalent of amino groups in the arylamine.

16. The process of claim 15 wherein the amount of catalyst is about 0.1 mol equivalent.

17. The process of claim 1 wherein the arylamine is reacted with about 5–40 mol equivalents of the olefin in the presence of about 1.25–1.5 mol equivalents of the alkyl nitrite, about 1–2 mol equivalents of the hydrogen halide, and about 0.05–0.2 mol equivalent of the catalyst per mol equivalent of amino groups in the arylamine.

18. The process of claim 17 wherein the amount of olefin is in the range of about 13–19 mol equivalents and the amount of catalyst is about 0.1 mol equivalent.

* * * * *